US 6,715,337 B2

(12) United States Patent
Huang et al.

(10) Patent No.: US 6,715,337 B2
(45) Date of Patent: Apr. 6, 2004

(54) NON-DESTRUCTIVE STRESS WAVE TESTING METHOD FOR WOOD

(75) Inventors: Yan-San Huang, Taipei (TW); Shin-Shin Chen, Taipei (TW)

(73) Assignee: Taiwan Forestry Research Institute, Taipei (TW)

( * ) Notice: Subject to any disclaimer, the term of this patent is extended or adjusted under 35 U.S.C. 154(b) by 0 days.

(21) Appl. No.: 10/295,946

(22) Filed: Nov. 18, 2002

(65) Prior Publication Data
US 2003/0094031 A1 May 22, 2003

(30) Foreign Application Priority Data
Nov. 20, 2001 (TW) .......................... 90128662 A

(51) Int. Cl.[7] .............................. G01M 7/08; G01N 3/30
(52) U.S. Cl. .......................... 73/12.12; 73/579; 73/597; 73/774
(58) Field of Search ................................ 73/597, 432.1, 73/12.01, 12.09, 12.12, 573, 579, 580, 581, 582, 583, 774, 775, 777, 778

(56) References Cited
U.S. PATENT DOCUMENTS

| 4,722,223 | A | * | 2/1988 | Bach et al. | ................ | 73/579 |
| 4,858,469 | A | * | 8/1989 | Hosgood et al. | ................ | 73/579 |
| 5,060,516 | A | * | 10/1991 | Lau et al. | ................ | 73/602 |
| 5,396,799 | A | * | 3/1995 | Ross et al. | ................ | 73/579 |
| 5,760,308 | A | * | 6/1998 | Beall et al. | ................ | 73/644 |
| 6,347,542 | B1 | * | 2/2002 | Larsson et al. | ........... | 73/12.12 |
| 6,598,477 | B2 | * | 7/2003 | Floyd | ........................ | 73/597 |

* cited by examiner

Primary Examiner—Hezron Williams
Assistant Examiner—Rose M. Miller
(74) Attorney, Agent, or Firm—Birch, Stewart, Kolasch & Birch, LLP

(57) ABSTRACT

A non-destructive stress wave testing method for wood. Two strain gauges are disposed on a timber. The timber is struck to generate an impact compression stress wave. The impact compression stress wave is measured by the strain gauges. An oscilloscope is provided to measure the time difference of the impact compression stress wave passing through the semiconductor strain gauges. The resonance frequency of the timber is sensed by the strain gauges and displayed on an FFT spectrum analyzer. Then, the speed of sound in the timber is determined according to the distance between the strain gauges and the time difference, or according to the length and the resonance frequency thereof. The strain gauges may be semiconductor strain gauges. The modulus of elasticity of the timber is determined according to the speed of sound therein and the density thereof.

13 Claims, 4 Drawing Sheets

US 6,715,337 B2

NON-DESTRUCTIVE STRESS WAVE TESTING METHOD FOR WOOD

This nonprovisional application claims priority under 35 U.S.C. §119(a) on Patent Application No. 90128662 filed in TAIWAN on Nov. 20, 2001, which is herein incorporated by reference.

BACKGROUND OF THE INVENTION

1. Field of the Invention

The invention relates to a stress wave testing method for wood, and more particularly to a non-destructive stress wave testing method for wood.

2. Description of the Related Art

Generally speaking, the moisture content, density and modulus of elasticity of wood can be measured by destructive and non-destructive testing methods. The non-destructive testing method means that the properties or inner structure of wood are measured without destroying the wood. For example, a positive linear relationship exists between the strength and the modulus of elasticity of wood. The strength of wood can be determined by the modulus of elasticity thereof. The techniques for measuring the modulus of elasticity include vibration, ultrasonic and stress wave methods. Further, a tap tone method is also provided to measure resonance frequency of wood according to the spectrum measured by an FFT spectrum analyzer. Then, the speed of sound in the wood and the modulus of elasticity of the wood can be determined according to the resonance frequency.

When one end of a timber is struck, stress waves generated therein are measured by a conventional non-destructive testing method. The conventional non-destructive testing method uses an acceleration transducer to measure the time difference of acceleration waveform between the two ends. Then, the speed of sound in the timber and the modulus of elasticity of the timber are determined according to the time difference. Nevertheless, the acceleration transducer is very expensive and easily damaged, thus reducing reliability thereof.

SUMMARY OF THE INVENTION

The present invention is directed to a non-destructive stress wave testing method for wood.

Accordingly, the present invention provides a non-destructive stress wave testing method for wood. A timber having a first end and a second end is provided. A first strain gauge and a second strain gauge are disposed on the first end and the second end, respectively. The first end of the timber is struck to generate an impact compression stress wave. The impact compression stress wave moves toward the second end of the timber along the longitudinal direction thereof and transforms into a tension stress wave on the second end to return to the first end, such that the impact compression stress wave moves between the first end and the second end. The resonance frequency of the timber is sensed by the first strain gauge and the second strain gauge. The time difference of the impact compression stress wave passing through the first strain gauge and the second strain gauge is measured by an oscilloscope. The resonance frequency of the timber is displayed on an FFT spectrum analyzer. Then, the speed of sound in the timber is determined according to the distance between the first and second strain gauges and the time difference, or according to the length and the resonance frequency thereof. The modulus of elasticity of the timber is determined according to the speed of sound therein and the density thereof.

DESCRIPTION OF THE DRAWINGS

For a better understanding of the present invention, reference is made to a detailed description to be read in conjunction with the accompanying drawings, in which.

DETAILED DESCRIPTION OF THE INVENTION

Figure 1:
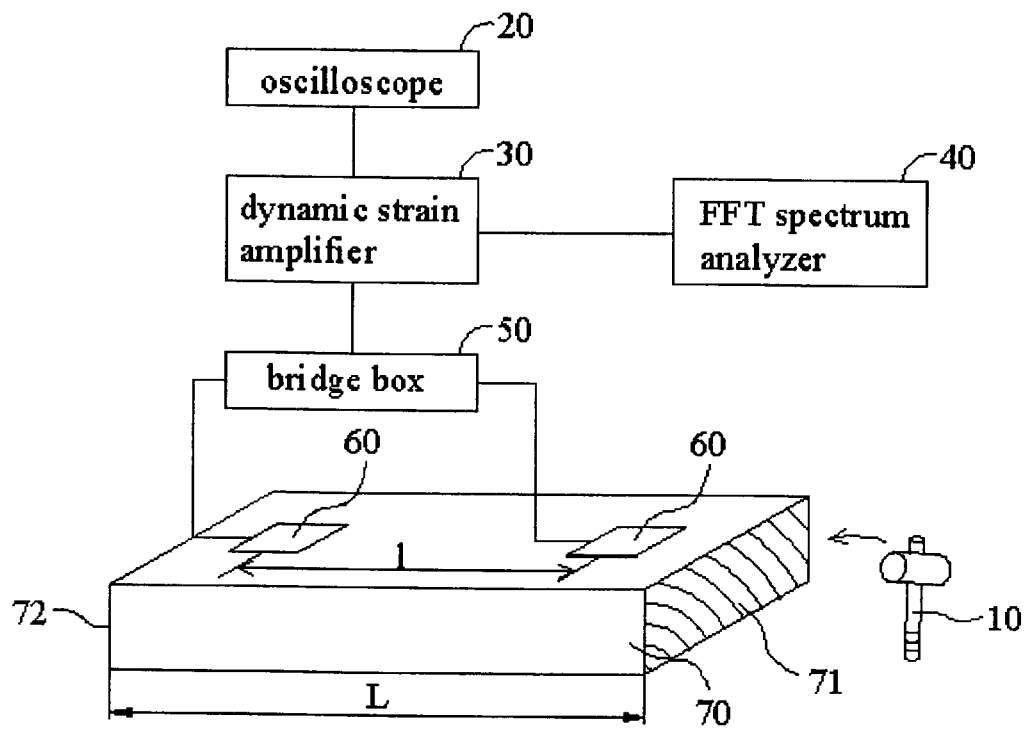
FIG. 1 is a schematic view showing the embodiment of the present invention.

Referring to FIG. 1, when the first end 71 of a timber 70 is struck by a hammer 10, an impact compression stress wave is generated on the first end 71 and moves toward the second end 72 of the timber 70 along the longitudinal direction thereof. The impact compression stress wave transforms into a tension stress wave on the second end 72 to return to the first end 71 along the longitudinal direction of the timber 70. The impact compression stress wave moves between the first end 71 and the second end 72 and at the speed of sound until the energy therein is exhausted by friction between the timber 70 and the impact compression stress wave. Meanwhile, the stress waves can be sensed by a semiconductor strain gauge 60.

The inner resistance of the semiconductor strain gauge 60 changes when the magnitude of the stress wave changes. When the inner resistance of the semiconductor strain gauge 60 changes, the voltage signal output by a bridge box 50 also changes. Meanwhile, the waveform of the voltage signal is identical to that of the stress wave. Additionally, since the voltage signal output by the bridge box 50 is very small, the voltage signal is amplified by a dynamic strain amplifier 30. Then, the amplified voltage signal is measured by an oscilloscope 20 and an FFT spectrum analyzer 40.

Figure 2:
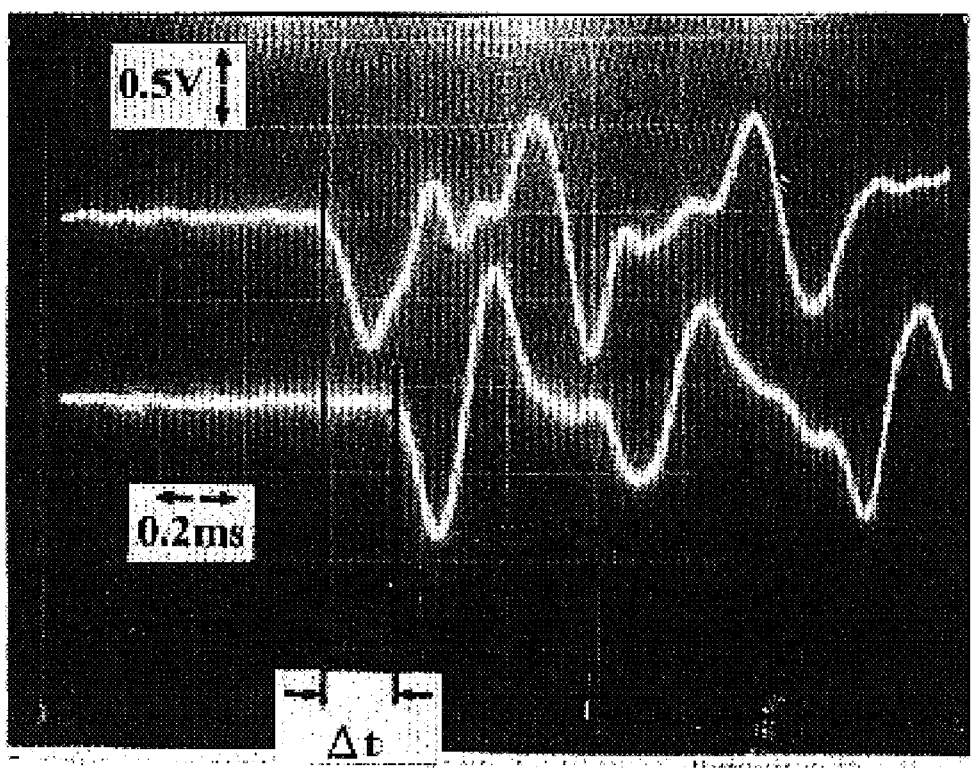
FIG. 2 shows the waveform of the stress wave measured by an oscilloscope.
Figure 3A:
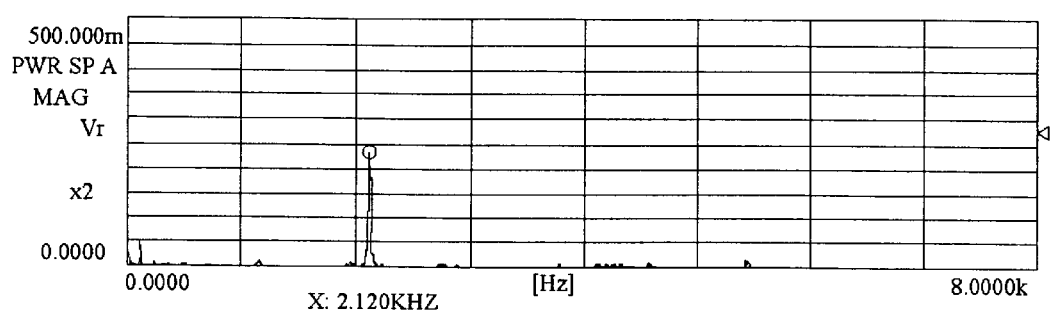
FIG. 3a shows the waveform of the stress wave measured by an FFT spectrum analyzer.
Figure 3B:
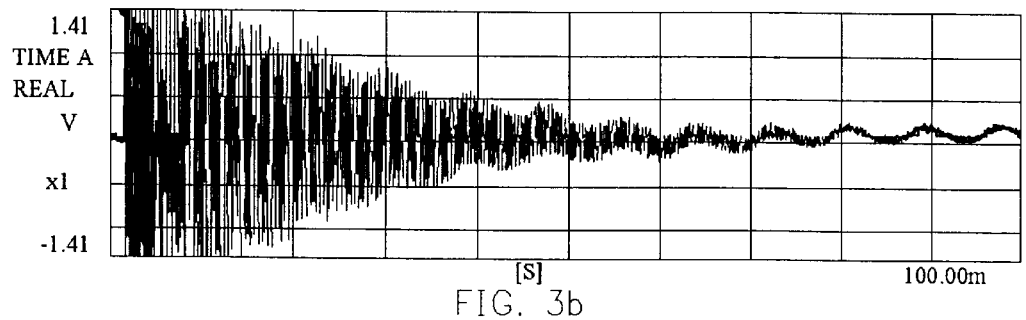
FIG. 3b shows the resonance frequency measured by an FFT spectrum analyzer.

Accordingly, the oscilloscope 20 can measure the time difference $\Delta t$ of the stress wave passing through the first strain gauge and the second strain gauge. The measurement is shown in FIG. 2. In addition, the waveform of the stress wave and the resonance frequency of the timber 70 can be sensed by the semiconductor strain gauges 60 and displayed on the FFT spectrum analyzer 40, as shown in FIG. 3a and FIG. 3b. According to the measurements shown in FIG. 3a and FIG. 3b, the main frequency of the stress wave sensed by the semiconductor strain gauges 60 is the same as that measured by the tap tone method.

As shown in FIG. 1, the semiconductor strain gauges 60 are attached on two opposite ends of the timber 70, respectively. As shown in FIG. 2, the waveform of the stress wave passing through the semiconductor strain gauges 60 are displayed on the oscilloscope 20. The speed of sound in the timber 70 can be determined as follows:

$$V = l/\Delta t,$$

wherein V denotes the speed of sound, l denotes the distance between the two semiconductor strain gauges 60, and $\Delta t$ denotes the time difference.

Then, the modulus of elasticity of the timber 70 can be determined as follows:

$$E=\rho V^2,$$

wherein E denotes the modulus of elasticity, and ρ denotes the density of the timber 70.

In addition, the waveform of the stress wave sensed by the semiconductor strain gauges 60 can be analyzed by the FFT spectrum analyzer 40 to obtain the resonance frequency $F_r$ of the timber 70. Since the resonance frequency $F_r$ is measured in such a way, it is not affected by environmental noise. The speed of sound in the timber 70 can also be determined as follows:

$$V=2F_r L,$$

wherein V denotes the speed of sound, and L denotes the length of the timber 70.

Then, the modulus of elasticity of the timber 70 can be determined as follows:

$$E=\rho V^2,$$

wherein E denotes the modulus of elasticity, and ρ denotes the density of the timber 70.

Figure 4A:
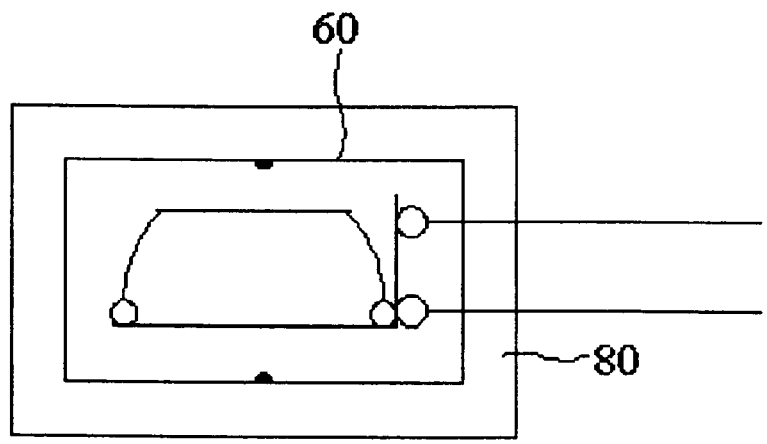
FIG. 4a is a top view showing the semiconductor strain gauge of the invention.
Figure 4B:
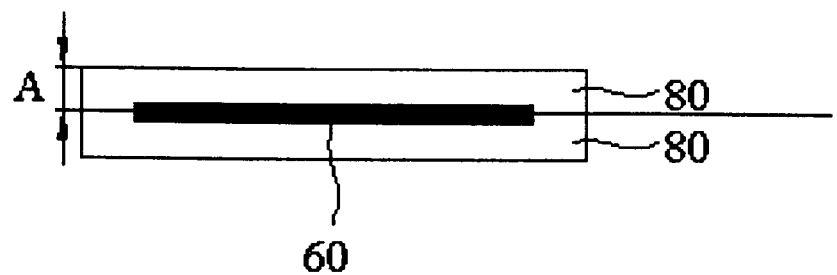
FIG. 4b is a side view showing the semiconductor strain gauge of the invention.

Conventionally, the strain gauges or semiconductor strain gauges are adhered to the timber 70, as shown in FIG. 1. After the stress wave test is finished, the semiconductor strain gauges are torn from the timber 70 and cannot be used any more. An additional benefit of the strain gauges or semiconductor strain gauges used in the present invention is that they can be reused to decrease testing costs. As shown in FIG. 4a and FIG. 4b, the semiconductor strain gauge 60 is covered by two cushioning elements 80 of resilient material such as resin whose thickness A is 0.5 mm. In other words, the semiconductor strain gauge 60 is inlaid or encased in the cushioning elements 80. When the timber 70 is tested, one side of a twin adhesive tape (not shown) is adhered to the timber 70. Then, the semiconductor strain gauge 60 in combination with the cushioning elements 80 is adhered to the other side of the twin adhesive tape. After the timber 70 is tested, the semiconductor strain gauge 60 in combination with the cushioning elements 80 can be torn from the twin adhesive tape without breakage. Thus, the semiconductor strain gauge 60 in combination with the cushioning elements 80 can be reused.

As shown in FIG. 1, according to experiments, when the size of the timber 70 is 100 mm (width)×100 mm (thickness)×1000 mm (length), the strain generated on the first end 71 approximates $50 \times 10^{-6}$. The gauge factor of a general strain gauge approximates 2. In order to enhance the gauge factor, the invention uses the semiconductor strain gauge 60 whose gauge factor approximates 120. Because sensitivity of the semiconductor strain gauge 60 is much higher, it can be used for measurement of larger timbers.

Accordingly, the invention uses the semiconductor strain gauge to sense the stress wave of the timber. The semiconductor strain gauge is cheaper and not easily damaged. The speed of sound in the timber and modulus of elasticity of the timber are determined according to the time difference of the stress wave measured by the oscilloscope and the resonance frequency measured by the FFT spectrum analyzer.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A non-destructive stress wave testing method for wood, comprising the steps of:

providing a timber having a first end and a second end;

disposing a first strain gauge and a second strain gauge on the first end and the second end, respectively;

striking the first end of the timber to generate an impact compression stress wave, wherein the impact compression stress wave moves toward the second end of the timber along the longitudinal direction thereof and transforms into a tension stress wave on the second end to return to the first end, such that the impact compression stress wave moves between the first end and the second end;

sensing the resonance frequency of the timber by the first strain gauge or the second strain gauge;

measuring the time difference of the impact compression stress wave passing through the first strain gauge and the second strain gauge by an oscilloscope; and displaying the resonance frequency of the timber on an FFT spectrum analyzer.

2. The non-destructive stress wave testing method for wood as claimed in claim 1, further comprising the steps of:

determining the speed of sound in the timber according to the distance between the first strain gauge and the second strain gauge and the time difference of the impact compression stress wave passing through the first strain gauge and the second strain gauge; and determining the modulus of elasticity of the timber according to the speed of sound therein and the density thereof.

3. The non-destructive stress wave testing method for wood as claimed in claim 2, wherein the formula for determining the speed of sound is: $V=l/\Delta t$, V denoting the speed of sound, l denoting the distance between the first strain gauge and the second strain gauge, and $\Delta t$ denoting the time difference.

4. The non-destructive stress wave testing method for wood as claimed in claim 3, wherein the formula for determining the modulus of elasticity is: $E=\rho V^2$, E denoting the modulus of elasticity, ρ denoting the density, and V denoting the speed of sound.

5. The non-destructive stress wave testing method for wood as claimed in claim 1, further comprising the steps of:

determining the speed of sound in the timber according to the length and the resonance frequency thereof; and determining the modulus of elasticity of the timber according to the speed of sound therein and the density thereof.

6. The non-destructive stress wave testing method for wood as claimed in claim 5, wherein the formula for determining the speed of sound is: $V=2F_r L$, V denoting the speed of sound, $F_r$ denoting the resonance frequency, and L denoting the length of the timber.

7. The non-destructive stress wave testing method for wood as claimed in claim 6, wherein the formula for determining the modulus of elasticity is: $E=\rho V^2$, E denoting the modulus of elasticity, ρ denoting the density, and V denoting the speed of sound.

8. The non-destructive stress wave testing method for wood as claimed in claim 1, further comprising a step wherein the first and second strain gauges are enclosed in at least one cushioning element comprising a resilient material such as resin.

9. The non-destructive stress wave testing method for wood as claimed in claim 1, further comprising a step wherein the first and second strain gauges are covered by at least one cushioning element comprising a resilient material such as resin.

10. The non-destructive stress wave testing method for wood as claimed in claim 1, wherein the first and second strain gauges are semiconductor strain gauges capable of changing a resistance therein according to the magnitude of the measured impact compression stress wave.

11. The non-destructive stress wave testing method for wood as claimed in claim 10, wherein the resistance in the first and second strain gauges is sensed by a bridge box and converted to a voltage signal, and the voltage signal is amplified by a dynamic strain amplifier and measured by the oscilloscope.

12. The non-destructive stress wave testing method for wood as claimed in claim 10, further comprising a step wherein the semiconductor strain gauges are enclosed in at least one cushioning element comprising a resilient material such as resin.

13. The non-destructive stress wave testing method for wood as claimed in claim 10, further comprising a step wherein the semiconductor strain gauges are covered by at least one cushioning element comprising a resilient material such as resin.

* * * * *